(12) United States Patent
Koest

(10) Patent No.: US 8,529,065 B2
(45) Date of Patent: Sep. 10, 2013

(54) ILLUMINATION SYSTEM AND METHOD

(75) Inventor: Gert Koest, Hannover (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 13/283,893

(22) Filed: Oct. 28, 2011

(65) Prior Publication Data

US 2012/0162605 A1 Jun. 28, 2012

(30) Foreign Application Priority Data

Oct. 28, 2010 (DE) .......... 10 2010 049 632
Sep. 8, 2011 (DE) .......... 10 2011 082 363

(51) Int. Cl.
*A61B 3/10* (2006.01)

(52) U.S. Cl.
USPC .......... 351/221; 351/212; 600/401

(58) Field of Classification Search
USPC .......... 351/200, 221, 212, 211, 213, 214, 351/246; 600/398, 399, 401
See application file for complete search history.

(56) References Cited

U.S. PATENT DOCUMENTS

| | | | |
|---|---|---|---|
| 4,834,527 A | 5/1989 | Kobayashi | |
| 5,002,056 A | 3/1991 | Takahashi et al. | |
| 5,131,739 A | 7/1992 | Katsuragi | |
| 5,751,395 A | 5/1998 | Thall | |
| 5,954,646 A | 9/1999 | Jost et al. | |
| 6,053,867 A | 4/2000 | Iijima | |
| 6,120,444 A | 9/2000 | Miyakawa et al. | |
| 2005/0174534 A1 | 8/2005 | Nakanishi | |
| 2006/0241367 A1* | 10/2006 | Koest | 600/405 |
| 2007/0097317 A1 | 5/2007 | Hayashi et al. | |
| 2009/0275820 A1 | 11/2009 | Miwa | |
| 2010/0097573 A1* | 4/2010 | Verdooner et al. | 351/206 |
| 2012/0065488 A1 | 3/2012 | Koest | |

FOREIGN PATENT DOCUMENTS

| | | |
|---|---|---|
| DE | 39 90 085 T1 | 1/1990 |
| DE | 3990085 C2 | 6/1994 |
| DE | 20 2005 002 562 U1 | 7/2005 |
| EP | 1779771 A1 | 2/2007 |
| EP | 2 095 761 A1 | 2/2009 |
| EP | 2113192 A1 | 11/2009 |

OTHER PUBLICATIONS

Search Report issued in corresponding European application 11 18 4914, completed Feb. 7, 2012 and mailed Feb. 16, 2012.

(Continued)

*Primary Examiner* — Darryl J Collins
*Assistant Examiner* — Gary O'Neill
(74) *Attorney, Agent, or Firm* — Griffin & Szipl., P.C.

(57) ABSTRACT

The invention relates to an illumination system (10) and an illumination method for an opthalmological analysis apparatus, in particular an analysis apparatus for measuring an intraocular pressure in an eye, wherein the analysis apparatus includes an actuation device (11) with which a puff of air for deforming a cornea (14) can be applied to the eye (12) in the direction of an optical axis (15) of the eye, wherein the illumination system includes at least one illumination device (23) with which the cornea of the eye can be illuminated by a slit light in such a way that a sectional image (27) can be generated in an illumination plane coinciding with the optical axis, wherein the illumination device is formed so that an illuminating beam path (28) of the illumination device oriented towards the eye is arranged at an angle α relative to the optical axis (15).

23 Claims, 4 Drawing Sheets

(56) References Cited

OTHER PUBLICATIONS

Merklinger, Harold M., "The Scheimpflug Principle—Part I," Shutterbug (Nov. 1992).
Stedman's Medical Dictionary 26th Ed. 1822 (1995), (Exhibit A).
Carmine D. Clemente, Gray's Anatomy, 30th American Edition, 1290 and 1291 (1985).
Ravi Thomas et al., How to Assess a Patient for Glaucoma, 19 Community Eye Health Journal 36-37 (2006).
Kathleen Romito, "Slit Lamp Exam for Glaucoma," at http://www.webmd.com/eye-health/slit-lamp-exam-for-glaucoma (last revised May 5, 2010).
Kathleen Romito, "Slit Lamp Examination," at http://www.peacehealth.org/xhtml/content/medicaltest/tu6231.html (last revised Jun. 9, 2011).
Robert Wilke et al., "Van Herick's Method for the Estimation of the Chamber Angle," at http://www.zeiss.com/C125679E00525939/EmbedTitelIntern/Van_Herick_en/$File/Van_Herick_en.pdf (downloaded Mar. 8, 2013), four pages.
Slit-lamp Exam, at http://health.allrefer.com/health/glaucoma-slit-lamp-exam.html (last reviewed Dec. 12, 2008).

* cited by examiner

ILLUMINATION SYSTEM AND METHOD

This application claims priority from German Patent Application No. 10 2010 049 632.4, filed Oct. 28, 2010, and from German Patent Application No. 10 2011 082 363.8, filed Sep. 8, 2011, the entire disclosures of which are incorporated herein by reference.

FIELD OF THE INVENTION

The invention relates to an illumination system for an opthalmological analysis apparatus and to an analysis apparatus having an illumination system, in particular, an analysis apparatus for measuring an intraocular pressure in an eye, wherein the analysis apparatus comprises an actuation device with which a puff of air for deforming a cornea can be applied to the eye in the direction of an optical axis of the eye, wherein the illumination system comprises at least one illumination device with which the cornea of the eye can be illuminated by a slit light in such a way that a sectional image can be generated in an illumination plane coinciding with the optical axis. The invention further relates to an illumination method for an opthalmological analysis apparatus.

BACKGROUND OF THE INVENTION

For example, such analysis systems can be formed as "non-contact tonometers", which can contactlessly deform a cornea of an eye by applying a puff of air by means of an actuation device. The actuation device may comprise a nozzle that is positioned approximately in the direction of an axis of vision of the eye. In order to measure an intraocular pressure in the eye, it is necessary to monitor a deformation caused by the puff of air. It is thus known to record this deformation using a monitoring system. For example, the monitoring system may capture a moment of retraction and expansion as well as a planar applanation of the cornea caused by the puff of air. The monitoring system is generally formed of a camera device, wherein the eye is illuminated during the deformation of the cornea using an illumination device so that the aforementioned stages of deformation can be derived from captured light reflections of the cornea. Illumination systems are also known in which the eye is illuminated so that sectional images of the undeformed and deformed cornea can be recorded by means of the camera device. In this case an illumination device is provided which projects a slit light onto the cornea in the direction of the optical axis of the eye. An area of the cornea illuminated by the slit light is visible as a sectional image, which can be recorded by a camera device arranged in an inclined manner beside the eye. In this case, there is the problem that an illumination of the cornea and of an illumination plane in the eye intersecting the axis of vision of the eye is obstructed by a position of the nozzle of the actuation device on the axis of vision. Although this can be counteracted by forming a transparent region around a nozzle opening and by projecting the slit light through the nozzle opening onto the eye, this is not a satisfactory solution since the slit light cannot be projected onto the eye directly, and therefore without interference. It is further necessary to arrange the actuation device, with the exception of the nozzle, outside the optical axis of the eye, which requires increased constructional outlay.

The object of the present invention is therefore to propose an illumination system for an opthalmological analysis apparatus, an analysis apparatus and an illumination method for an analysis apparatus with which an illumination quality can be improved and which is easy to produce and use.

SUMMARY OF THE INVENTION

This object of the invention is achieved by an illumination system having the features in accordance with a first embodiment, an analysis apparatus having the features in accordance with a tenth embodiment, and an illumination method having the features in accordance with a sixteenth embodiment, of the invention. In accordance with the first embodiment of the invention, an illumination system (10, 38) for an opthalmological analysis apparatus, in particular an analysis apparatus for measuring an intraocular pressure in an eye, is provided, wherein the analysis apparatus includes an actuation device (11, 39) with which a puff of air for deforming a cornea (14) can be applied to the eye (22) in the direction of an optical axis (15, 45) of the eye, and the illumination system includes at least one illumination device (23, 40) with which the cornea of the eye can be illuminated by a slit light (25) in such a way that a sectional image (27) can be generated in an illumination plane (26) coinciding with the optical axis, wherein the illumination device is formed so that an illuminating beam path (28, 43) of the illumination device oriented towards the eye is arranged at an angle α relative to the optical axis (15, 45).

In accordance with a second embodiment of the present invention, the first embodiment is modified so that the illumination system (10, 38) comprises two illumination devices (23, 40) that can illuminate the illumination plane (26). In accordance with a third embodiment of the present invention, the second embodiment is further modified so that the illumination devices (23, 40) are arranged coaxially to the optical axis (15, 45). In accordance with a fourth embodiment of the present invention, the first embodiment, the second embodiment and the third embodiment are further modified so that the illumination device (23, 40) comprises a filter means that can compensate for differences in brightness of a sectional image (27).

In accordance with a fifth embodiment of the present invention, the fourth embodiment is further modified so that the filter means forms at least one graduated filter. In accordance with a sixth embodiment of the present invention, the fifth embodiment is further modified so that the graduation filter can shade the illuminating beam path (28, 43) centrally. In accordance with a seventh embodiment of the present invention, the fifth embodiment or the sixth embodiment is further modified so that the graduation filter may continuously shade the illuminating beam path (28, 43) transverse to the slit light (25). In accordance with an eighth embodiment of the present invention, the first embodiment, the second embodiment, the third embodiment, the fourth embodiment, the fifth embodiment, the sixth embodiment, and the seventh embodiment are further modified so that a light means of the illumination device (23, 40) is formed of at least one light-emitting diode (30). In accordance with a ninth embodiment of the present invention, the first embodiment, the second embodiment, the third embodiment, the fourth embodiment, the fifth embodiment, the sixth embodiment, the seventh embodiment, and the eighth embodiment, are further modified so that the illumination device (40) comprises a deflection means (42) by means of which the illuminating beam path (43) can be deflected in the illumination device by an angle β.

In accordance with a tenth embodiment of the present invention, an opthalmological analysis apparatus for measuring an intraocular pressure in an eye is provided, wherein the opthalmological analysis apparatus includes an illumination system (10, 38) according to any one of the first embodiment, the second embodiment, the third embodiment, the fourth embodiment, the fifth embodiment, the sixth embodiment, the seventh embodiment, the eighth embodiment and the ninth embodiment, wherein the analysis apparatus comprises an actuation device (11, 39) with which a cornea (14) of the eye (12) can be deformed, wherein a puff of air for deforming the cornea can be applied to the eye using the actuation device in the direction of an optical axis (15, 45) of the eye, wherein the analysis apparatus comprises a monitoring system (13) with which the deformation of the cornea can be monitored and recorded, and wherein sectional images (27) of the undeformed and deformed cornea can be recorded using the monitoring system. In accordance with an eleventh embodiment of the present invention, the tenth embodiment is modified so that the illumination system (10, 38) is spatially independent of the actuation device (11, 39).

In accordance with a twelfth embodiment of the present invention, the tenth embodiment or the eleventh embodiment is further modified so that an illumination device (23, 40) of the illumination system (10, 38) is pivotable by an angle α relative to an apparatus axis of the actuation device (11, 39) or the optical axis (15, 45). In accordance with a thirteenth embodiment of the present invention, the tenth embodiment, the eleventh embodiment, and the twelfth embodiment are further modified so that the monitoring system (13) comprises a camera device (32, 33) with which the sectional images (27) can be recorded, and the camera device and the illumination system (10, 38) being arranged in such a way that the camera device and the sectional image are arranged in a Scheimpflug arrangement. In accordance with a fourteenth embodiment of the present invention, the tenth embodiment, the eleventh embodiment, the twelfth embodiment and the thirteenth embodiment are further modified so that the actuation device (11, 39) comprises a transparent plate (22) in which an opening (21) for outputting the puff of air is formed, and an illuminating beam path (28, 43) of the illumination system (10, 38) is able to penetrate through the plate. In accordance with a fifteenth embodiment of the present invention, the tenth embodiment, the eleventh embodiment, the twelfth embodiment, the thirteenth embodiment, and the fourteenth embodiment, are further modified so that the analysis apparatus is formed in such a way that the monitoring system (13), together with the illumination system (10, 38), can be rotated about an apparatus axis of the actuation device (11, 39) or the optical axis (15, 45) of the eye.

In accordance with a sixteenth embodiment of the present invention, an illumination method for an opthalmological analysis apparatus, in particular an opthalmological analysis apparatus for measuring an intraocular pressure in an eye, is provided, wherein the opthalmological analysis apparatus includes an illumination system (10, 38), and the opthalmological analysis apparatus includes an actuation device (11, 39) with which a puff of air for deforming a cornea (14) is applied to the eye (12) in the direction of an optical axis (15, 45) of the eye, and the illumination system comprises at least one illumination device (23, 40) with which the cornea of the eye is illuminated by a slit light (25), a sectional image (27) being generated in an illumination plane (26) coinciding with the optical axis, characterised in that an illuminating beam path (28, 43) of the illumination device is oriented towards the eye at an angle α relative to the optical axis (15, 45).

In the illumination system according to the invention for an opthalmological analysis apparatus, in particular an analysis apparatus for measuring an intraocular pressure in an eye, the opthalmological analysis apparatus comprises an actuation device with which a puff of air for deforming a cornea can be applied to the eye in the direction of an optical axis of the eye, wherein the illumination system comprises at least one illumination device with which the cornea of the eye can be illuminated by a slit light in such a way that a sectional image can be generated in an illumination plane coinciding with the optical axis, and wherein the illumination device is formed in such a way that an illuminating beam path of the illumination device oriented towards the eye is arranged at an angle α relative to the optical axis or axis of vision of the eye.

It is thus provided to arrange the illumination device laterally beside a nozzle of the actuation device so that a sectional image in the eye can, nevertheless, be generated in an area of the illumination plane lying in the axis of vision, a beam path of the illumination device no longer being obstructed by the actuation device or the nozzle, however. The slit light or illuminating beam path must lie in the illumination plane coinciding with the optical axis so that a maximum deformation of the cornea can be captured. This is made possible because the illumination plane is oriented towards the puff of air. A quality of the illumination and, therefore, of the sectional images can be noticeably improved by the lateral arrangement of the illumination device. It is further possible to also arrange the actuation device completely in the direction of the optical axis, for example, without a curved nozzle feed being necessary. On the whole, the actuation device can thus also be formed in a more compact manner. A further advantage of the laterally inclined arrangement of the illumination device is that the person to be examined is exposed to reduced glare since the light incident into the eye is not projected directly into a central area of a retina of the eye.

It is particularly advantageous if the illumination system comprises two illumination devices, which can illuminate the illumination plane. It can thus be ensured that there is no undesired shadowing of edge regions of the cornea by one illumination device alone. Further improved sectional images can also be obtained since, due to angles of incident light, which may be different, of the different illuminating beam paths of the illumination device, an improved light scattering within the optical medium of the cornea can be achieved. Particles found on or in the cornea can also be illuminated by the use of two illumination devices so that an undesired particle shadowing is illuminated, at least in part, or eliminated. It is also possible to generate a sectional image in a particularly large area of the cornea by using two such illumination devices.

The illumination devices may also be arranged coaxially to the optical axis. A coaxial and, therefore, relatively opposed arrangement, based on the optical axis, of the illumination devices thus affords the advantage that the illuminating beam paths can be matched particularly well to one another. In particular, a superimposition of the beam paths in the region of the cornea is thus necessary.

It is particularly advantageous if the illumination device comprises a filter means, which can compensate for differences in brightness of a sectional image. Differences in brightness of a sectional image may be caused, for example, if, with an illuminating beam path incident into the cornea in a laterally inclined manner, one portion of the illuminating beam path travels over a longer path through the cornea than another portion. With the aid of the filtering means, the part of the illuminating beam path that causes a lighter sectional image can be shaded so that the sectional image appears to be of uniform brightness overall.

For example, the filter means may form at least one graduated filter. Using a graduation filter, a sectional image can be shaded in areas thereof, which might appear too light in a particularly simple manner.

The graduation filter may be formed so that it can shade the illuminating beam path centrally. In particular, if two illumination devices are used, it is possible to form particularly light areas in the sectional image in the region of the coinciding illuminating beam paths within the cornea of the eye. Such a graduation filter makes it possible to shade these coinciding areas.

Alternatively or in addition, the graduation filter may continuously shade the illuminating beam path transverse to the slit light. A course of the illuminating beam path transverse thereto ranging from light to dark can thus be achieved. In particular, with such a graduation filer the laterally inclined incidence of the illuminating beam path into the eye can be considered and any deviations in brightness of the sectional image can be corrected.

A light means of the illumination device can be formed of at least one light-emitting diode. The light-emitting diode may be arranged in the illumination device together with one or more lenses and/or screens to form the illuminating beam path. Furthermore, it is also conceivable to use a plurality of light diodes arranged in a row to form the slit light.

The illumination device may also comprise a deflection means, such as a prism or a mirror, by means of which the illuminating beam path can be deflected in the illumination device by an angle β. For example, the angle β may be 90° so that a housing of the illumination device can be arranged transverse to the illumination plane. As a result of the deflection means, it is possible to form or arrange the illumination device or a housing thereof so that the analysis apparatus can be formed in a compact manner.

The opthalmological analysis apparatus according to the invention for measuring an intraocular pressure in an eye comprises an illumination system according to the invention, wherein the analysis apparatus comprises an actuation device with which a cornea of the eye can be deformed, wherein a puff of air for deforming the cornea can be applied to the eye using the actuation device in the direction of an optical axis of the eye, wherein the analysis apparatus comprises a monitoring system with which the deformation of the cornea can be monitored and recorded, wherein sectional images of the undeformed and deformed cornea can be recorded using the monitoring system. It is thus possible, using an analysis means of an analysis apparatus, to derive the intraocular pressure from the sectional images of the cornea. The intraocular pressure can be determined particularly precisely since sectional images of high optical quality can be obtained by using the illumination system according to the invention. Since the sectional images are evaluated in terms of a course of deformation using the analysis means, the course of deformation can consequently be established particularly precisely.

If the illumination system is spatially independent of the actuation device then any influence on the illumination device or on the illumination system by an optionally mechanical drive of the actuation device can be ruled out. A replacement or maintenance and calibration of the illumination system can also be carried out independently of the analysis system because the illumination system can be exchanged in a particularly simple manner.

An illumination device of the illumination system may also be pivotable by an angle α relative to an apparatus axis of the actuation device and the optical axis of the eye. It is thus possible to adjust an angle of incidence into the eye of the illuminating beam path relative to the optical axis, as appropriate. The angle of incidence may be adapted to specific requirements of a measurement.

It is advantageous if the monitoring system comprises a camera device with which the sectional images can be recorded, and wherein the camera device and the illumination system are arranged in such a way that the camera device and the sectional image are arranged in a Scheimpflug arrangement in accordance with the Scheimpflug principle. Photos of the sectional images, which are equalised, can thus be obtained by means of the camera device. This makes it possible to directly measure lengths and positions from the sectional images, without having to use further correcting calculations.

In order to protect an eye against damage caused by a nozzle of the actuation device in the event of a possible collision with the actuation device, the actuation device may comprise a transparent plate in which an opening for outputting the puff of air is formed, wherein an illuminating beam path of the illumination system can penetrate through the plate. The transparent plate can thus surround the nozzle to such an extent and form a nozzle opening that any damage to the eye caused by sharp components is prevented. Depending on the size of the plate, the illuminating beam path or illuminating beam paths of the illumination system can be directed through the transparent plate and onto the eye.

Furthermore, the analysis apparatus can be formed in such a way that the monitoring system, together with the illumination system, can be rotated about an apparatus axis of the actuation device or the optical axis of the eye. It is thus possible to obtain sectional images of the different respective angles of rotation, as a result of which a three-dimensional model of the relevant area of the eye can be derived from the sectional images using the analysis means. In particular, the compact design of the actuation device enabled by the illumination system facilitates the formation of such an analysis apparatus. The monitoring system and the illumination system can thus rotate freely about the apparatus axis because the actuation device can be formed along the optical axis.

Further advantageous embodiments of an analysis apparatus will emerge from the description of features of the various embodiments of the present invention.

In the illumination method according to the invention for an opthalmological analysis apparatus having an illumination system, in particular an opthalmological analysis apparatus for measuring an intraocular pressure in an eye, the opthalmological analysis device comprises an actuation device with which a puff of air for deforming a cornea can be applied to the eye in the direction of an optical axis of the eye, wherein the illumination system comprises at least one illumination device with which the cornea of the eye is illuminated by a slit light, wherein a sectional image is generated in an illumination plane coinciding with the optical axis, wherein an illuminating beam path of the illumination device is oriented towards the eye at an angle α relative to the optical axis. In terms of the advantages afforded by the illumination method according to the invention, reference is made to the description of advantages regarding the illumination system according to the invention.

Further advantageous embodiments of the illumination method will emerge from the description of features of the various embodiments of the invention.

BRIEF SUMMARY OF THE DRAWINGS

A preferred embodiment of the invention will be described in greater detail hereinafter with reference to the accompanying drawings, in which.

DETAILED DESCRIPTION OF THE INVENTION

Figure 1:
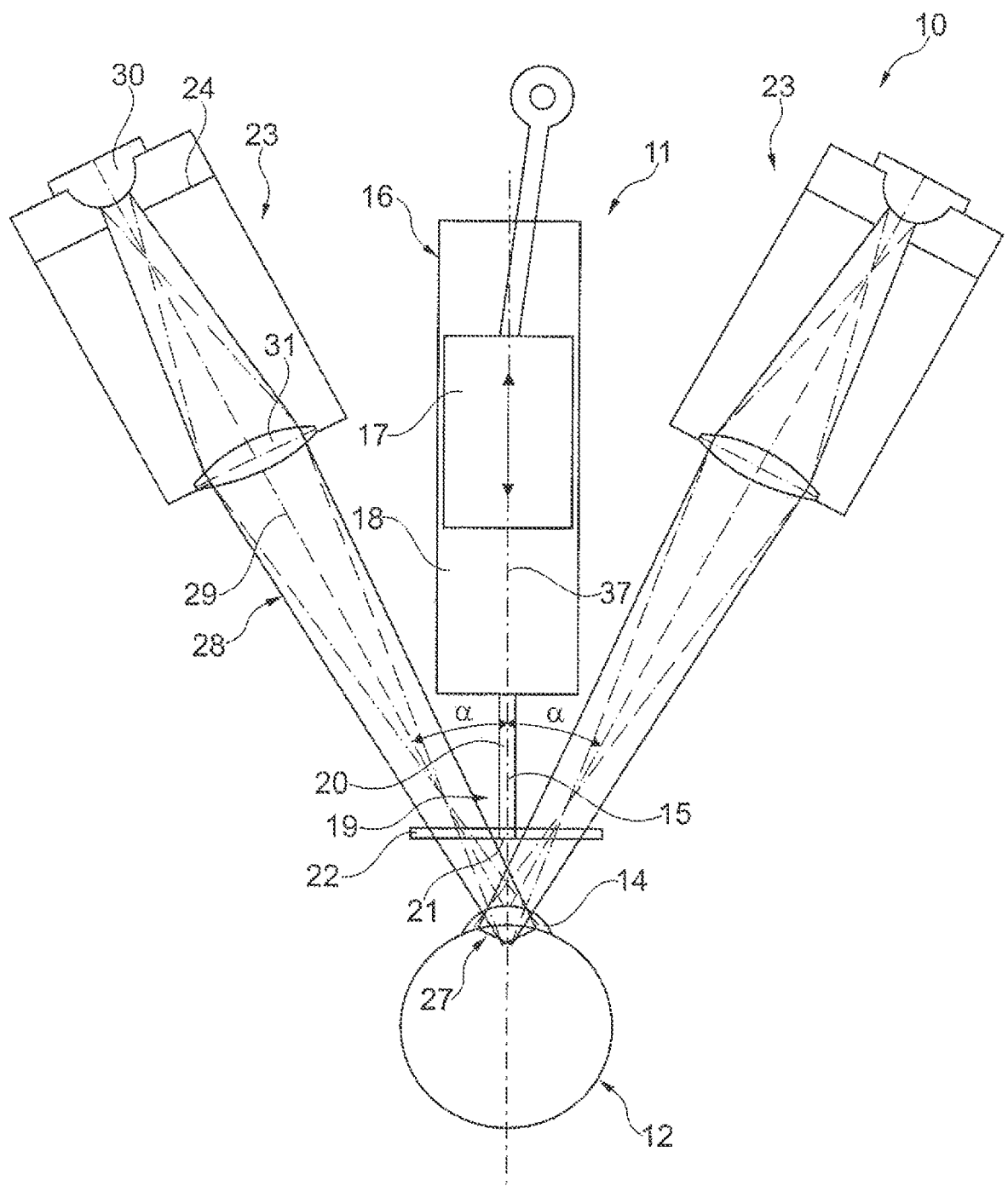
FIG. 1 is a schematic plan view of an analysis apparatus in accordance with the present invention.
Figure 2:
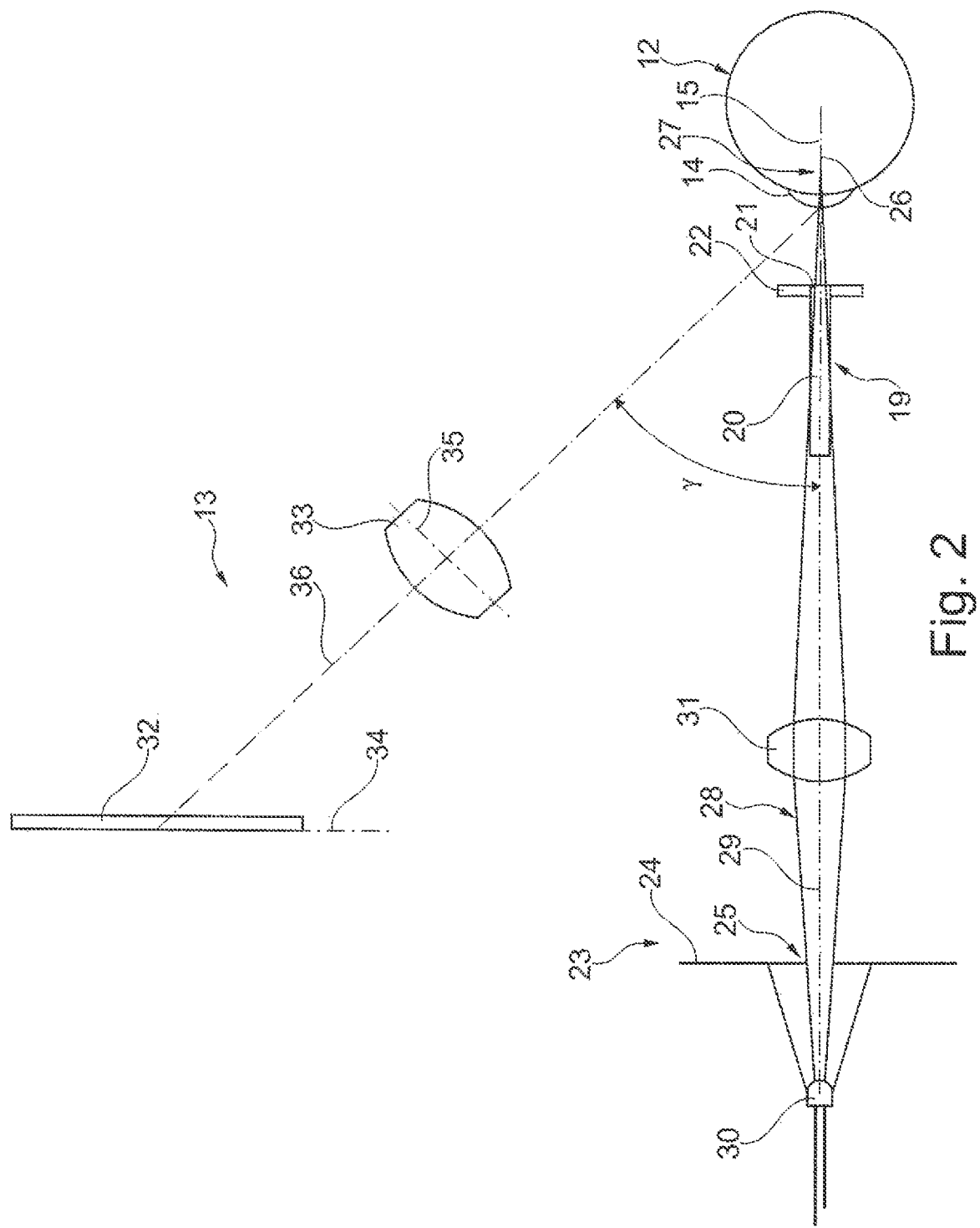
FIG. 2 is a schematic side view of the analysis apparatus in accordance with the present invention.

Viewed together, FIGS. 1 and 2 show an illumination system 10 having an actuation device 11 (shown in part) of an analysis apparatus (not shown in more detail than its components) and an eye 12. In particular in FIG. 2, a monitoring system 13 of the analysis apparatus can also be seen. The analysis apparatus measures an intraocular pressure in the eye 12, wherein a puff of air for deforming a cornea 14 of the eye 12 is applied to the eye 12 using the actuation device 11 in the direction of an optical eye 15 of the eye 12. The actuation device 11 is basically formed of a reciprocating pump 16 with a drive (not shown here in greater detail), and a piston 17, which is arranged so as to be longitudinally movable in a cylinder 18, as well as a nozzle 19. The nozzle 19 comprises a nozzle duct 20, a nozzle opening 21 and a transparent plate 22 in which the nozzle opening 21 is formed. The actuation means 11 is basically arranged along the optical axis 15.

The illumination system 10 comprises two illumination devices 23 that illuminate the cornea 14 using a slit light 25 generated using a screen 24 so that a sectional image 27 is generated in an illumination plane 26 coinciding with the optical axis 15. An illuminating beam path 28, or the optical axis 29 thereof, of the illumination device 23 is arranged at an angle α relative to the optical axis 15 of the eye 12. The illumination devices 23 basically each comprise a light-emitting diode 30 as a light source and a lens 31 for adapting the illumination beam path 28. The illumination devices 23 are arranged relative to the actuation device 11 so that the respective illuminating beam paths 28 pass through the transparent plate 22 into the eye 12 and superimpose one another in the region of the cornea 14 and generate the sectional image 27.

The sectional image 27 is recorded by means of the monitoring system 13, which is also only shown schematically here. The monitoring system 13 is formed of a camera (not shown in greater detail) with an image sensor 32 and an objective lens 33. The image sensor 32 forms a projection plane 34 which, together with an objective plane 35 and the illumination plane 26, are arranged as an image plane in accordance with the Scheimpflug principle. In the present example an optical axis 36 of the monitoring system 13 is arranged at an angle γ relative to the illumination plane 26, wherein the optical axis 36 lies with the optical axis 15 in a cross-sectional plane 37.

Figure 3:
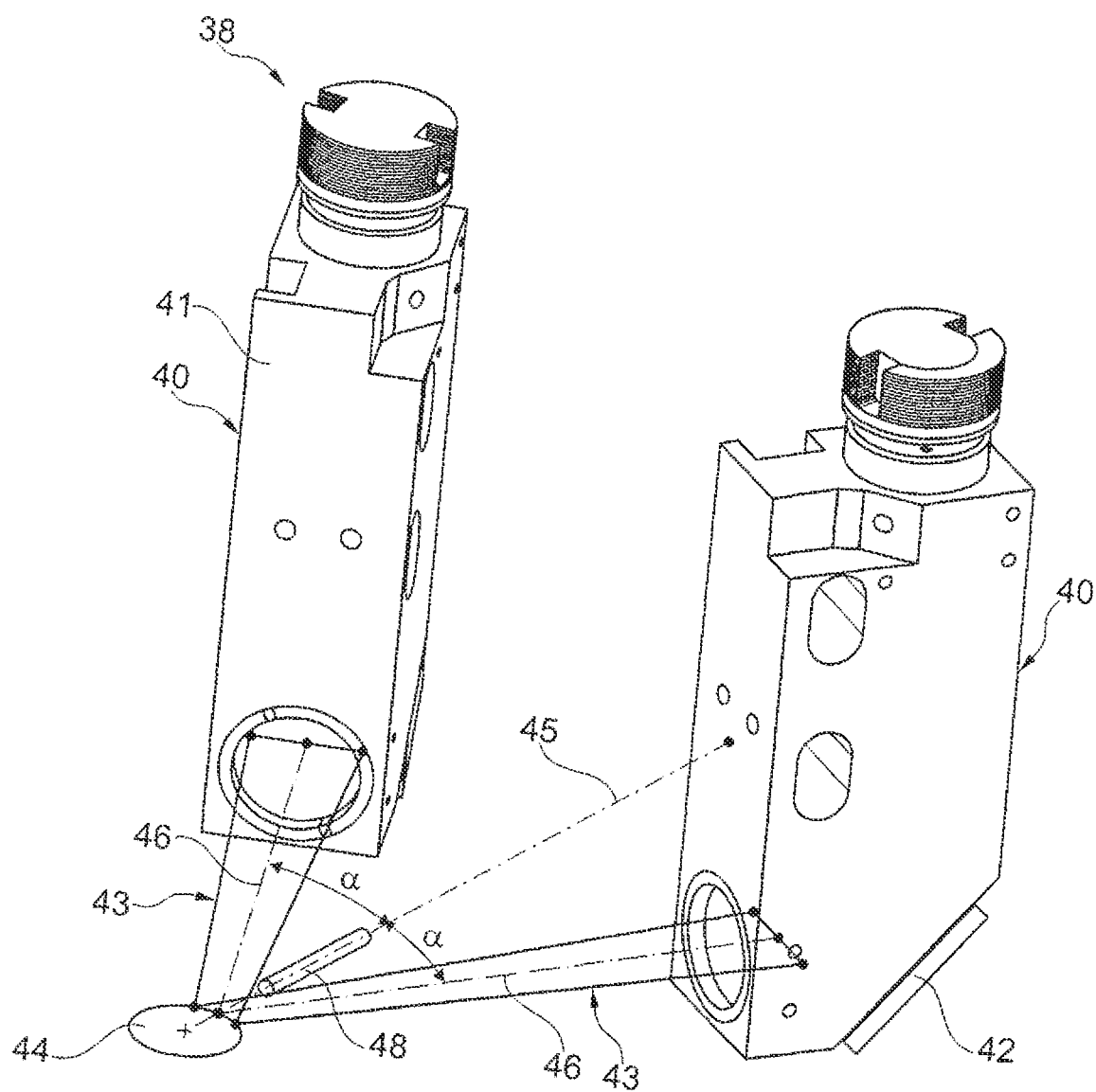
FIG. 3 is a perspective view of an illumination system in accordance with the present invention.
Figure 4:
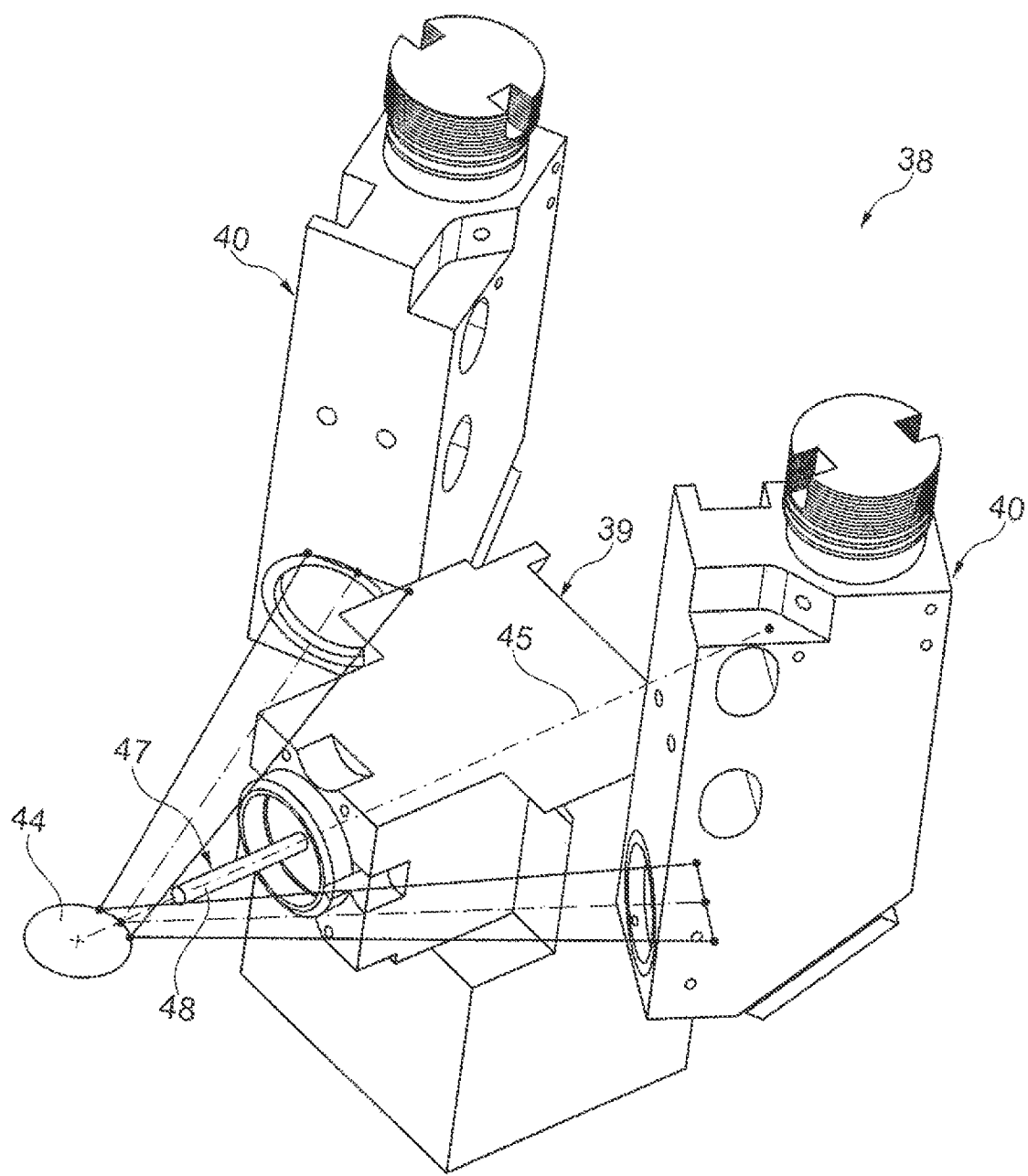
FIG. 4 is a perspective view of the illumination system together with an actuation device of the present invention.

Viewed together, FIGS. 3 and 4 show an illumination system 38 in different perspective illustrations, wherein in FIG. 4 an actuation device 39 is additionally shown. The illumination system 38 basically consists of two identical illumination devices 40 with a housing 41 and a light source (not visible in greater detail here than by the illuminating beam path 43 originating from each light source) as well as a deflecting means formed as a mirror 42 for deflecting an illuminating beam path 43 onto an eye 44. The illuminating beam path 43 is deflected at an angle of approximately 90°. The illumination devices 40 are arranged relative to an optical axis 45 of the eye 44 so that an optical axis 46 of the illuminating beam path 43 forms an angle α with the optical axis 45 of the eye 44 and therefore the actuation device 39 can still be arranged between the two illumination devices 40 in front of the eye 44 with a nozzle 47. A nozzle duct 48 of the nozzle 47 is aligned with the optical axis 45 of the eye 44.

The invention claimed is:

1. An illumination system associated with an ophthalmological analysis apparatus, in particular an opthalmological analysis apparatus for measuring an intraocular pressure in an eye, wherein the analysis apparatus comprises an actuation device that applies a puff of air that deforms a cornea of the eye in a direction of an optical axis of the eye, wherein the illumination system comprises:
   (a) at least one illumination device that illuminates the cornea of the eye by a slit light so that a sectional image of the cornea is generated in an illumination plane coinciding with the optical axis of the eye, wherein the at least one illumination device is constructed so that an illuminating beam path of the at least one illumination device oriented towards the eye is arranged at an angle a relative to the optical axis of the eye.

2. The illumination system associated with the ophthalmological analysis apparatus according to claim 1, wherein the illumination system comprises two illumination devices disposed to illuminate the illumination plane, wherein each of the two illumination devices illuminates the illumination plane along a separate illuminating beam path oriented towards the eve at an angle α relative to the optical axis of the eye.

3. The illumination system associated with the ophthalmological analysis apparatus according to claim 2, wherein the two illumination devices are arranged coaxially to the optical axis of the eye.

4. The illumination system associated with the ophthalmological analysis apparatus according to claim 2, wherein each illumination device comprises a filter means that compensates for differences in brightness of the sectional image.

5. The illumination system associated with the ophthalmological analysis apparatus according to claim 4, wherein the filter means forms at least one graduated filter.

6. The illumination system associated with the ophthalmological analysis apparatus according to claim 5, wherein the at least one graduated filter is disposed to shade the illuminating beam path centrally.

7. The illumination system associated with an ophthalmological analysis apparatus according to claim 6, wherein the graduated filter continuously shades the illuminating beam path transverse to the slit light.

8. The illumination system associated with the ophthalmological analysis aparatus according to claim 2, wherein the two separate illuminating beam paths corresponding to the two illumination devices are oriented at an angle of 2α relative to each other.

9. The illumination system associated with the ophthalmological analysis apparatus according to claim 5, wherein the graduated filter continuously shades the illuminating beam path transverse to the slit light.

10. The illumination system associated with the ophthalmological analysis apparatus according to claim 1, wherein the at least one illumination device includes a light means comprising at least one light-emitting diode.

11. The illumination system associated with the ophthalmological analysis apparatus according to claim 1, wherein the at least one illumination device comprises a deflection means disposed to deflect the illuminating beam path in the at least one illumination device by an angle β.

12. An ophthalmological analysis apparatus operable to measure an intraocular pressure in an eye, the ophthalmological analysis apparatus comprising:

(a) an illumination system comprising at least one illumination device that illuminates a cornea of the eye by slit light so that a first sectional image of the cornea is generated in an illumination plane coinciding with an optical axis of the eye, wherein the at least one illumination device is constructed so that an illuminating beam path of the at least one illumination device oriented towards the eye is arranged at an angle α relative to the optical axis of the eye;

(b) an actuation device operable so as to deform the cornea of the eye, wherein a puff of air that deforms the cornea is applied to the eye using the actuation device in a direction of an optical axis of the eye; and (c) a monitoring system operable so deformation of the cornea is monitored and recorded, and wherein second sectional images of the undeformed and deformed cornea are recorded using the monitoring system.

13. The ophthalmological analysis apparatus according to claim 12, wherein the illumination system is spatially independent of the actuation device.

14. The ophthalmological analysis apparatus according to claim 13, wherein an illumination device of the illumination system is pivotable by an angle α relative to an apparatus axis of the actuation device or relative to the optical axis of the eye.

15. The ophthalmological analysis apparatus according to claim 12, wherein an illumination device of the illumination system is pivotable by an angle α relative to an apparatus axis of the actuation device or relative to the optical axis of the eye.

16. The ophthalmological analysis apparatus according to claim 12, wherein the monitoring system comprises a camera device operable to record the second sectional images of the cornea of the eye, and the camera device and the illumination system are arranged so that the camera device and the first sectional image of the cornea are arranged in a Scheimpflug arrangement.

17. The ophthalmological analysis apparatus according to claim 12, wherein the actuation device comprises a transparent plate in which an opening for outputting the puff of air is formed, and the illuminating beam path of the illumination system is disposed to penetrate through the transparent plate.

18. The ophthalmological analysis apparatus according to claim 12, wherein the analysis apparatus is constructed so that the monitoring system, together with the illumination system, are rotatable about an apparatus axis of the actuation device or about the optical axis of the eye.

19. The ophthalmological analysis apparatus according to claim 12, wherein the illumination system comprises two illumination devices disposed to illuminate the cornea of the eye by slit light so that the first sectional image of the cornea is generated in the illumination plane coinciding with the optical axis of the eye, wherein each of the two illumination devices is constructed to orient a separate illuminating beam path towards the eye, and each of the separate illuminating beam paths is arranged at an angle α relative to the optical axis of the eye.

20. The ophthalmological analysis apparatus according to claim 19, wherein the two separate illuminating beam paths corresponding to the two illumination devices are oriented at an angle of 2α relative to each other.

21. An illumination method for an ophthalmological analysis apparatus, in particular an ophthalmological analysis apparatus for measuring an intraocular pressure in an eye, wherein the ophthalmological analysis apparatus comprises (a) an illumination system;
(b) an actuation device with which a puff of air for deforming a cornea is applied to the eye in the direction of an optical axis of the eye; and
(c) at least one illumination device with which the cornea of the eye is illuminated by slit light, wherein the method comprises the steps of:
  i. generating a sectional image of the cornea in an illumination plane coinciding with the optical axis of the eye using the at least one illumination device; and
  ii. orienting an illuminating beam path of the at least one illumination device towards the eye at an angle α relative to the optical axis of the eye.

22. The illumination method according to claim 21, wherein the ophthalmological analysis apparatus comprises two illumination devices with which the cornea of the eye is illuminated by slit light, and wherein the sectional image of the cornea in the illumination plane coinciding with the optical axis of the eye is generated using the two illumination devices, and a separate illuminating beam path of each of the two illumination devices is oriented towards the eye at the angle α relative to the optical axis of the eye.

23. The illumination method according to claim 22, wherein the two separate illuminating beam paths corresponding to the two illumination devices are oriented at an angle of 2α relative to each other.

\* \* \* \* \*